(12) United States Patent
Feingold

(10) Patent No.: US 7,207,998 B2
(45) Date of Patent: Apr. 24, 2007

(54) INTRACORNEAL LENS PLACEMENT METHOD AND APPARATUS

(75) Inventor: Vladimir Feingold, Laguna, CA (US)

(73) Assignee: Biovision AG, Brugg (CH)

( * ) Notice: Subject to any disclaimer, the term of this patent is extended or adjusted under 35 U.S.C. 154(b) by 864 days.

(21) Appl. No.: 10/618,279

(22) Filed: Jul. 11, 2003

(65) Prior Publication Data

US 2004/0097955 A1 May 20, 2004

Related U.S. Application Data

(60) Division of application No. 09/586,273, filed on Jun. 2, 2000, now Pat. No. 6,599,305, which is a continuation-in-part of application No. 09/132,987, filed on Aug. 12, 1998, now Pat. No. 6,083,236.

(51) Int. Cl.
*A61F 9/00* (2006.01)
(52) U.S. Cl. .................................................. 606/166
(58) Field of Classification Search ................ 606/166, 606/107, 169; 623/6.12, 5.11, 906
See application file for complete search history.

(56) References Cited

U.S. PATENT DOCUMENTS 6,596,006 B1 *   7/2003   Hanna ........................ 606/166
6,623,498 B1 *   9/2003   Ziemer ....................... 606/166

* cited by examiner

Primary Examiner—Kevin T. Truong
(74) Attorney, Agent, or Firm—Lawrence S. Cohen

(57) ABSTRACT

A method and apparatus for correcting vision, including a corneal-pocket keratome device to create a corneal pocket and a lens to be inserted and retained in the corneal pocket to effect correction. The corneal-pocket keratome includes a drive unit having cutting head elements which contact the subject eye during corneal pocket formation. The cutting head elements may be removeable and may be disposable. The cutting head elements include a corneal restraint device, which may be a positioning ring to position an eyeball with the cornea protruding through the ring; a keratome blade assembly with a corneal-pocket blade; and may also include an applanation shoe surface to restrain the cornea, in addition or instead of the positioning ring. The applanation shoe may be pivotable away from the surgical area. The corneal-pocket blade may include a guide which travels with the blade. The blade assembly oscillates laterally while extending forward into the cornea to form the pocket, and the amplitude of the lateral oscillation is preferably increased as the blade goes beyond an opening incision into the cornea. Lenses for this invention preferably include a feature to impede accidental lens movement after the lens is disposed within the corneal pocket, which may be a swelling after insertion or a circumferential irregularity. Lenses may be of Fresnel or non-Fresnel type, and may employ annular changes in the index of refraction of the lens material, as well as changes in refractive shape which may be annular or not, to effect variations in focal length for relieving presbyopia, astigmatism, and combinations of those as well as myopia and hyperopia. Drive control and vacuum for the positioning ring are provided under user command by a control unit having user inputs.

16 Claims, 14 Drawing Sheets

INTRACORNEAL LENS PLACEMENT METHOD AND APPARATUS

The present application is a divisional of application Ser. No. 09/586,273 filed on Jun. 2, 2000 now U.S. Pat. No. 6,599,305 which is a continuation-in-part of application Ser. No. 09/132,987 filed on Aug. 12, 1998 now U.S. Pat. No. 6,083,236 issued on Jul. 4, 2000 the contents of all of which are incorporated herein by reference.

FIELD OF THE INVENTION

The present invention pertains to the general field of ophthalmologic surgery, and in particular to surgical methods and devices for corneal implantation of optical lenses.

BACKGROUND

Numerous ophthalmic surgical procedures have been developed for correcting imperfect visual acuity such as myopia or hyperopia. A variety of keratomes have been developed over recent decades, devices for performing corneal resectioning to permit access to inner portions of the cornea, where surgical reshaping may then be used to permanently correct vision defects.

Referring to FIGS. 1 and 2a, a typical prior art resectioning operation will separate flap 6 of corneal (and epithelial) tissue 2 from eyeball 4. The outer layers of cornea and epithelial cells are separated and lifted away to expose the inner layers 12 of cornea 2, and are left attached only as flap 6. Exposed interior layers 12 of cornea 2 will to some extent adjust themselves, or their shape may be altered through further surgical steps, such as laser ablation or subsequent resectioning, to remove a contoured layer of corneal tissue. At the conclusion of the surgical procedure, flap 6 is typically replaced over inner corneal tissues 12 to protect the healing tissues.

However, most such surgical reshaping is not reversible, resulting in some risk of creating permanent visual aberrations for the patient. A known alternative is to surgically prepare an opening in the cornea of an eye having visual abnormalities, and to insert a lens therein. Such surgery is difficult to perform accurately. Moreover, the lenses which are available for such vision correction are not entirely satisfactory for a variety of reasons, including a tendency to shift out of position after placement, to impair transcorneal gas diffusion, to be excessively thick, or to be unable to correct presbyopia or astigmatism.

Accordingly, there exists a need for a method and device for correcting visual abnormalities through surgical implantation of an appropriate corrective lens within the cornea an eye in such a way that the lens may be reliably placed and will remain properly positioned and oriented, to enable reversible correction of a wide range of visual abnormalities.

SUMMARY OF THE INVENTION

The present invention solves the above-noted need by providing a method and devices for intracorneal lens placement. A specially adapted lens is implanted in a corneal pocket which has been precisely formed by a device which creates and shapes the pocket to accept and retain a lens in the cornea. Whereas in typical corrective surgery an entire flap of the cornea is lifted as shown in FIG. 2a to permit access for further surgical modification of the cornea, in vision modification according to the present invention a flap of cornea is not lifted, but rather a pocket is formed in the corneal tissue as shown in FIG. 2b. As much of the corneal surface as practical is left intact to simplify healing and to discourage movement or loss of the inserted lens.

In order to position a lens within the cornea of an eye in a precisely predictable and repeatable manner, and to help retain the intended orientation and positioning of the lens while the eye heals from surgery, the present invention provides a corneal pocket keratome to create a pocket of precise dimensions in the cornea, and also a lens having special features to establish a close fit between the lens and the corneal pocket. Both of these pieces can be realized in a number of different embodiments. Moreover, the corneal pocket keratome has several subparts, each of which can be realized in many ways.

The lens size and shape matches the corneal pocket formed by the corneal pocket keratome, and provides desired focal modifications when disposed within corneal tissue. The lens permits sufficient gas diffusion to allow adequate oxygenation of internal eye tissues. In preferred embodiments, lens features create an interference fit between the lens and the corneal tissue at the edges of the corneal pocket to aid in retaining the placement and orientation of the lens. In addition to a precise fit, such retention features of the lens may include a material which swells when hydrated after placement within the cornea, or variations in the radius of the lens to form circumferential bumps. The lens may accordingly have an asymmetric, radially and/or axially varying focus to compensate for the effects of astigmatism or presbyopia, generally in addition to compensation for myopia or hyperopia. For some applications, lens thickness may be desirably reduced by employing a Fresnel intracorneal lens.

The corneal pocket keratome preferably includes a surgical unit having cutting head elements mounted on a keratome drive assembly, and also a control unit and a footpedal. During formation of a pocket in the cornea, the cutting head elements are in intimate contact with the subject eye, either to position the eye or to create an incision. The control unit supplies power and vacuum to control the surgical unit according to settings entered by the user, and in response to commands made using the footpedal. The surgical unit is preferably hand-held and easily positioned over the subject eye.

The preferred surgical unit may include four distinct elements. Three of these are "cutting head" elements which contact the eye during corneal surgery—a positioning ring assembly, a corneal support assembly, and a corneal pocket blade assembly. Preferably, each of these three cutting head elements extends from the fourth element, a keratome drive assembly, which drives the corneal pocket blade assembly with respect to the other two cutting head elements in such a way that interference and rubbing between parts of the corneal pocket keratome is minimal or entirely absent near the surgical site. It is also preferred that each of the three cutting head elements is easily removed and as easily replaced onto the fourth element, the drive assembly, without a need for tools, so the surgeon can ensure sterility by simply replacing the cutting head elements. Ease of replacement also enables the surgeon to readily select different styles and sizes of cutting head elements, as desired for a particular operation.

The subject eye is held in a position by a positioning device, which is typically a positioning ring attached to the keratome drive assembly. The positioning ring is supplied with vacuum which draws the eye into the ring causing the cornea to protrude through the ring. Then, in most applications the protruded cornea is pressed against a corneal support assembly which is also attached to the keratome drive assembly. The corneal pocket blade assembly is attached to a driving member of the keratome drive assembly such that a corneal pocket blade of the assembly is positioned near the corneal support assembly. Upon direction from the operator, the keratome drive unit imparts a compound movement to the corneal pocket blade through the driving member, driving the blade forward into the cornea while also causing the blade to oscillate laterally.

The blade preferably travels within a cutting plane which is controlled with respect to the corneal surface. The corneal surface is typically disposed against the corneal support assembly. The precise position of the cutting plane with respect to the corneal surface may be controlled by a guide which is supported by, and travels along with, the corneal pocket blade assembly and directly contacts the cornea. Alternatively, the cutting plane may be maintained at a known distance from the corneal support assembly. The distance may be controlled by a guide portion of the corneal pocket blade assembly which interferes with the corneal support assembly during cutting. Such interfering guide, if used, may contact the cornea or may be positioned to avoid such contact. The cutting plane to corneal support distance may also be controlled directly by the mechanical connection between the corneal support surface, the keratome drive assembly, and the corneal pocket blade assembly. By thus controlling the cutting plane with respect to a reference plane of the corneal support assembly, contours may be formed in the corneal support assembly which will translate into variations in the depth of the pocket below the corneal surface, thus controlling the shape of the formed pocket.

For some applications, it is desirable to practice the invention omitting the corneal support assembly, leaving only the positioning ring and the corneal pocket blade assembly in intimate contact with the subject eye. In this event the positioning ring is stationary with respect to the subject eye, while the corneal pocket blade is driven with respect thereto. In embodiments thus omitting the corneal support assembly, the thickness of the cut is preferably controlled by a guide which is part of the corneal pocket blade assembly and is in direct contact with the corneal surface tissue.

A feature of some embodiments of the present invention is a pivotable corneal support assembly, which may be swung out of the way while the eye is retained by the positioning ring to permit examination and treatment of the eye with minimal disturbance of the surgical setup.

In order to allow insertion of the lens, and yet facilitate its retention, the corneal pocket keratome preferably creates a pocket having an opening in the corneal surface tissue which is narrower, measured laterally to the direction of the cut, than the maximum lateral width of the pocket which accommodates the widest part of the lens. This is accomplished in the preferred embodiment by increasing the amplitude of the lateral oscillation imparted to the corneal pocket blade as the blade moves farther into the corneal tissue.

BRIEF DESCRIPTION OF THE DRAWINGS

FIG. 8b is a section view of FIG. 8a.

FIG. 10b shows a releasable locking method for the applanator of FIG. 10a.

FIG. 11b shows details of positioning ring restraint at section 11b–11b of FIG. 11a.

DETAILED DESCRIPTION

The present invention presents means to permanently, yet reversibly, correct defects of vision by disposing a lens in a pocket in a cornea. Various embodiments correct myopia, hyperopia, astigmatism, presbyopia, or a combination of these defects. Appropriate lenses are provided, as well as a device to create a corneal pocket to accept these lenses. The correction may be permanent, if it remains satisfactory, and may also be reversed by removing the lens from the cornea.

Figure 1:
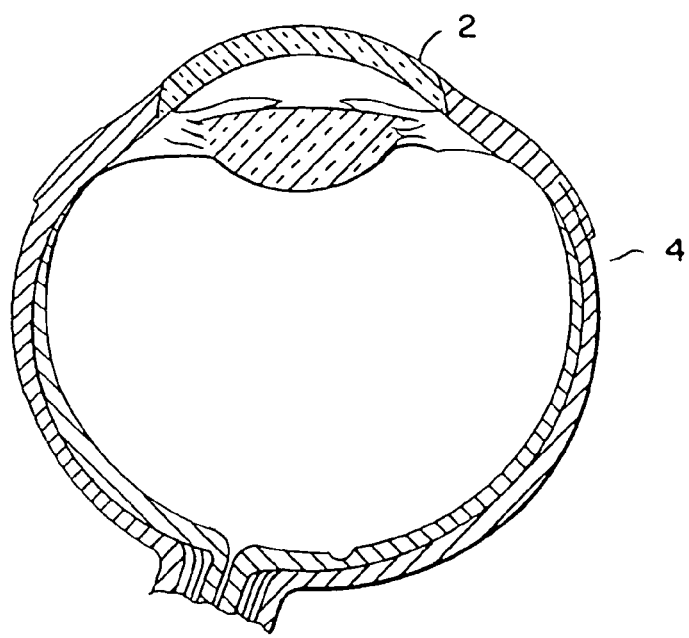
FIG. 1 is a cross-section of an eye.
Figure 2A:
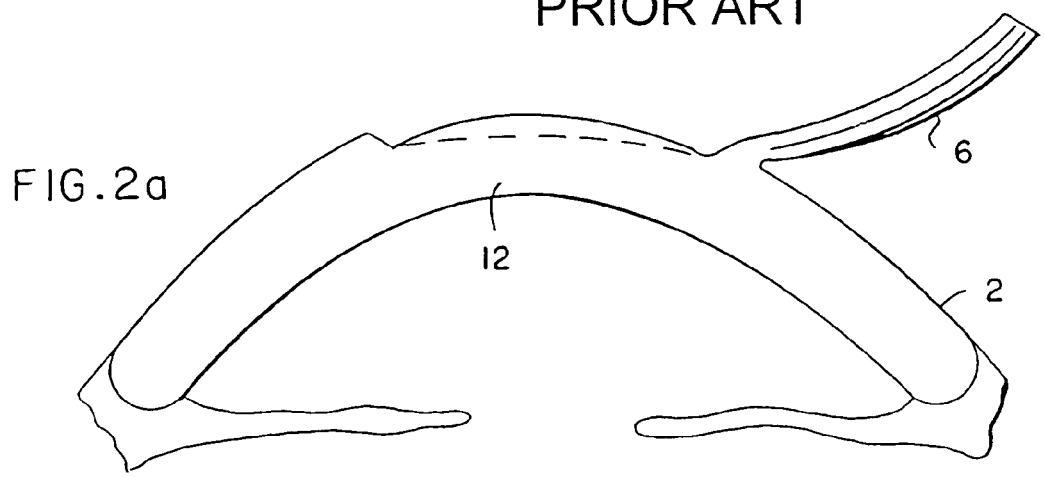
FIG. 2a shows a cornea with a flap of epithelial tissue lifted as in the prior art.
Figure 2B:
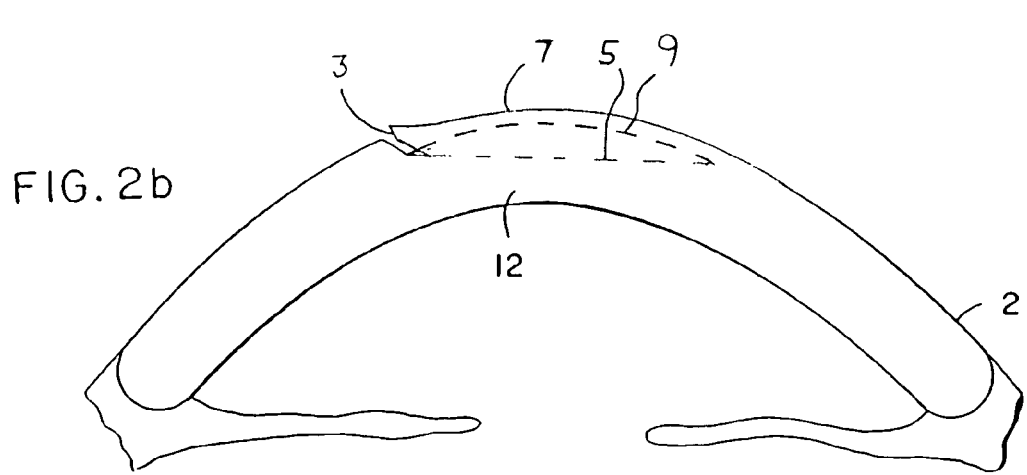
FIG. 2b shows a cornea with a pocket formed below the epithelial tissue.
Figure 3:
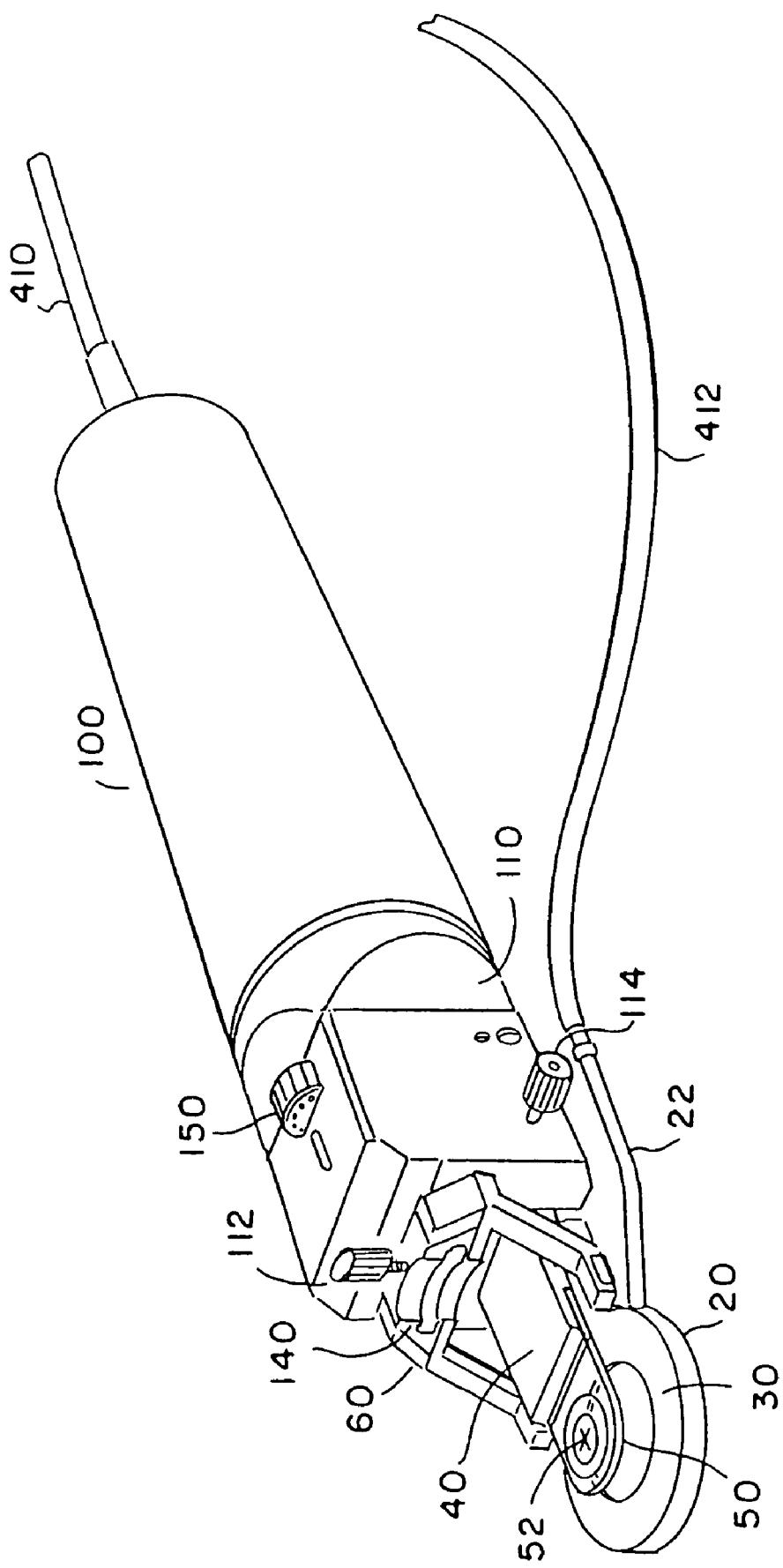
FIG. 3 shows a surgical unit for the invention, with cutting head elements on a drive assembly.
Figure 4:
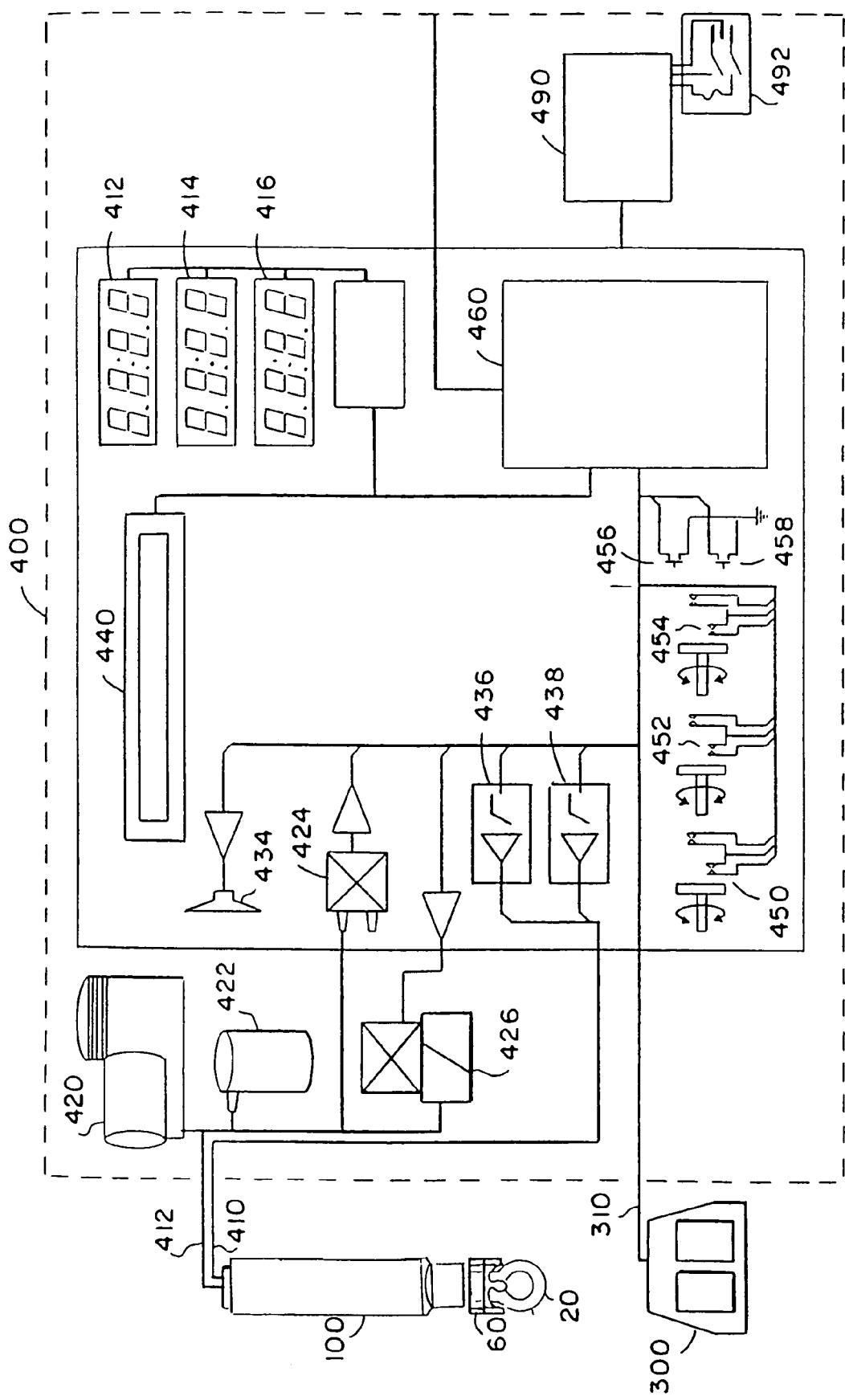
FIG. 4 shows the control unit with connections to the surgical unit and to a foot pedal.
Figure 5:
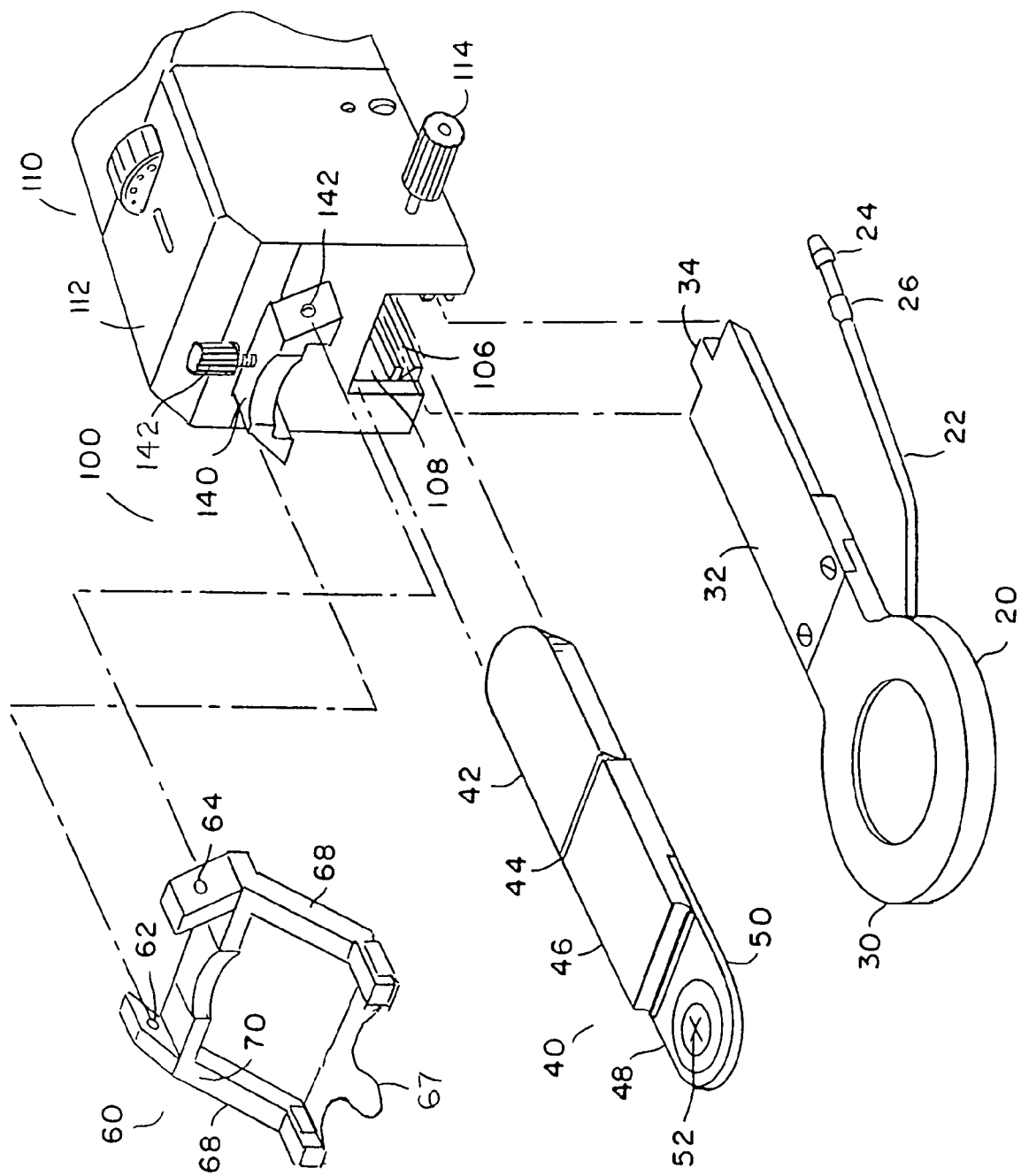
FIG. 5 shows the surgical unit front with cutting head elements disengaged therefrom.

We begin with an overview of a device for preparing a corneal pocket to retain an appropriate lens in a subject eye. Referring to FIGS. 3, 4 and 5, such a device is preferably embodied in three separate components: surgical unit 100, footpedal 300, and control unit 400. Surgical unit 100 has four subsections including drive assembly 110 and three cutting head elements: positioning ring assembly 20, optional applanator assembly 40, and blade fork assembly 60. Footpedal 300 communicates user commands to control unit 400 via cable 310, and surgical unit 100 is connected to control unit 400 by electrical cable 410 and vacuum hose 412. Each of these items are discussed in more detail below.

Control Unit

Electrical and vacuum control are preferably provided by control unit 400 as shown in FIG. 4. Control unit 400 is a microprocessor-controlled unit enabling the user to direct operation of the actuators within drive assembly 110 and the level of vacuum supplied to positioning ring assembly 20 of surgical unit 100. The user may control operation, for example, by means of two pedal switches included in footpedal 300, in conjunction with three rotary input devices 450, 452 and 454 and two pushbuttons 456 and 458 on the front panel of control unit 400. Operating parameters are displayed on the front panel for the user by means of numeric readouts 412, 414 and 416 and by multiple character alpha-numeric display 440, while speaker 434 gives audible information.

A microprocessor on printed circuit board 460 executes operating firmware which is held in reprogrammable non-volatile memory and can be reprogrammed in the field. The firmware allows the microprocessor system to read switch closures and the rotation of the rotary controls. These electronics translate operator actions into tool control voltages which are applied to the drive unit actuators and can be stored as presets to be recalled as required by the operator. The microprocessor system also interprets the sensors and controls the actuators to maintain vacuum at a level set by the user.

Control unit 400 provides electric control signals to surgical unit 100 via cable 410. Vacuum pressure for positioning ring assembly 20 is supplied from control unit 400 via vacuum hose 412. Control unit 400 contains vacuum reservoir 422 in which vacuum pressure is established by vacuum pump 420 and released by vacuum release solenoid 426, and the vacuum pressure is sensed by vacuum transducer 424 to give feedback to the control electronics. Electric control for the actuators (not shown) within drive assembly 110 is provided by electronic switches 436–438. Persons skilled in the art will appreciate that there is no limit to the variations by which control unit components may control the surgical unit actuators and vacuum.

Surgical Unit

Referring to FIG. 3, surgical unit 100 includes drive assembly 110 for supporting and driving three cutting head elements which contact the eye during surgery. The cutting head elements include positioning ring assembly 20, applanator assembly 40, and blade fork assembly 60. Surgical unit 100 is supplied electrically via cable 410, and vacuum is supplied to positioning ring 30 via vacuum hose 412 which attaches to vacuum connection tube 22.

FIG. 5 clearly delineates the three cutting head elements, including positioning ring assembly 20, applanator assembly 40 (not used in all embodiments), and blade fork assembly 60, as they are separated from drive assembly 110. Since each of these cutting head elements ordinarily comes into direct contact with an eye being operated upon, it is preferable that they be easily removable from, and replaceable on, drive assembly 110, in order to facilitate the use of clean and sterile elements. For the same reason, it is also preferable that these cutting head elements be either sterilizable or sterile disposable.

Blade fork 70, and blade support 65 which is suspended from blade fork arms 68, are all part of blade fork assembly 60. Blade support 65 in turn supports (or may be one part with) blade 67. Blade fork 70 is connected to blade fork drive arm 140 which impels the entire blade fork assembly 60. A dove-tail or trapezoidal attachment mechanism between blade fork 70 and blade fork drive arm 140 is shown. Threaded spring-ball assembly 64 in blade fork 70 causes a ball to press into a complementary detent, not shown, in drive arm 140 to properly position blade fork 70 to drive arm 140. The attachment mechanism may be made removeable with a thumbscrew 142, as shown, or by other means.

Blade fork 70 is preferably composed of titanium but many other materials are suitable, including stainless steel. For a steam sterilizable blade fork, dimensionally stable plastics such as polycarbonate or polysulfone are suitable, and gas or gamma ray sterilization is compatible with additional plastics, such as polypropylene.

Surgical Cutting Action

FIGS. 6a–6d show the cutting head elements in use resectioning cornea 2. Vacuum pressure delivered to vacuum chamber 36 of positioning ring 30 will draw sclera 3 and cornea 2 of eye 4 upward such that cornea 2 is retained, and in applanator embodiments is pressed against applanation shoe 50. In the embodiment shown in FIG. 6a, blade fork arm 68 supports blade 67 so the blade travels in a plane between positioning ring 30 and applanation shoe 50, but without contacting either ring 30 or shoe 50. Blade fork drive arm 140 (FIG. 5) supports the blade fork assembly 70 (FIG. 5) of which blade fork arm 68 is a part, and imparts a compound movement to it. Blade fork assembly 70 is oscillated in a direction parallel to the cutting edge of blade 6 (in and out of the page of FIGS. 6a–6d), and simultaneously moved slowly forward (from right to left in FIGS. 6a–6d), while maintaining blade 67 at a controlled distance from applanation shoe 50. Blade 67 thereby enters into cornea 2 and creates a pocket below that layer of corneal tissue 2 which is positioned between the plane of travel of blade 67 and the near surface of applanation shoe 50. The forward travel of blade fork arm 70 continues until the formation of the pocket is completed. In this embodiment, blade 67 is guided without using a guide, as in FIG. 8k.

Figure 7:
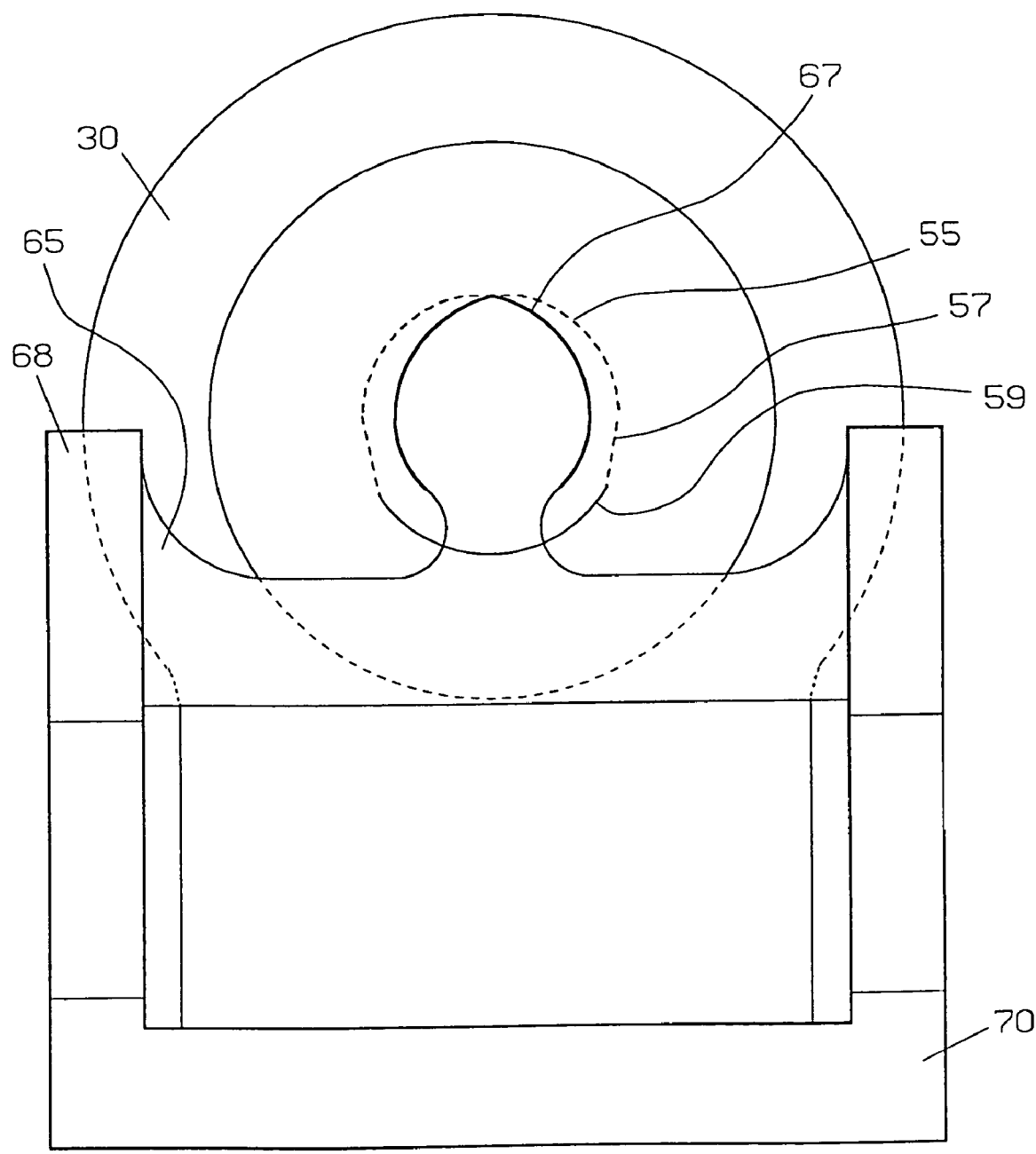
FIG. 7 is a top view of a blade in a corneal pocket of an eye retained by a positioning ring.

FIG. 7 is a top view of corneal pocket 56. Blade fork assembly 70 has blade fork arms 68 which suspend blade support 65. Blade 67, in this case, is of a piece with blade support 65. Cornea 2 is held by positioning ring 30. Blade 67 has entered into the corneal tissue, opening incision line 59, and has proceeded into the cornea. Blade 67 is oscillated laterally—left and right in FIG. 7—while it is simultaneously driven into cornea 2 (vertically ascending in FIG. 7) at least until it reaches the point shown. As blade 67 traveled into cornea 2 from incision line 59 to the position shown, the amplitude of the lateral oscillation of the blade was increased gradually, until the blade lateral oscillation amplitude is maximum in the position shown, where it defines the widest portion of pocket 56. Entry channel edges 57 of pocket 56 are closer together at incision line 59 and farther apart when they join pocket circumferential edge 55. (The small flat region of the pocket shown at the tip of blade 67 can be substantially eliminated, if desired, by progressively reducing the amplitude of the lateral oscillation of the blade while moving the blade slightly farther into cornea 2.) The narrowing channel for lens insertion formed between edges 57 discourage an inserted lens from slipping out of cornea 2.

Corneal Pocket Wall Thickness Control

It is clearly desirable to precisely control the thickness of corneal epithelial tissue which remains above the pocket. Generally, a constant thickness of pocket wall is desired, except in some cases of corneal irregularities. Returning to FIGS. 6a–6d, four embodiments are shown which each control pocket wall thickness in a different manner.

Figure 6A:
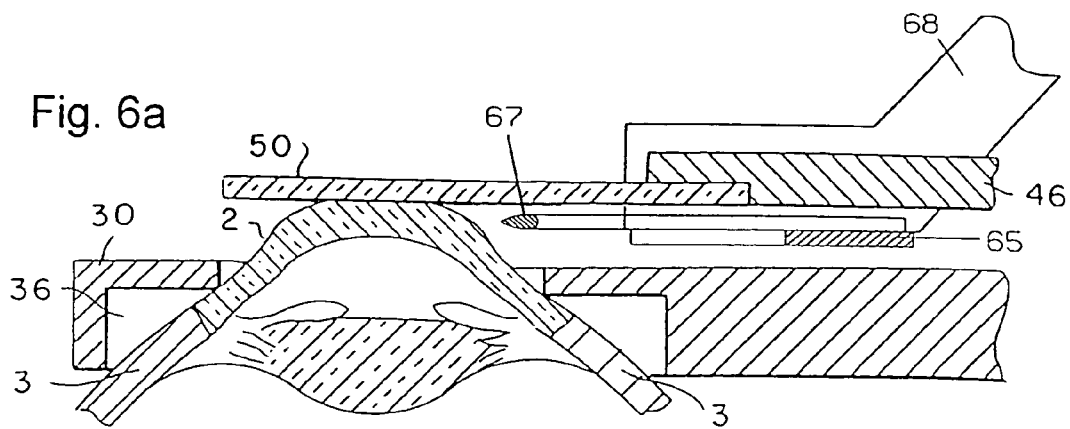
FIG. 6a shows an eyeball held against the applanator shoe by the positioning ring, and a blade supported by a blade fork prepared to cut a corneal pocket.

In FIG. 6a, precise control of the spacing between applanator shoe 50 and blade 67 is maintained during the cut. The position of blade 67 is preferably maintained within 0.050 mm, and even more preferably within 0.030 mm, of a selected distance from a surface reference plane of applanation shoe 50. In the presence of a guide (e.g. 63, 69) this distance from blade 67 is preferably maintained within 0.5 mm and even more preferably within 0.1 mm or less, but tolerances even larger than 0.5 mm may be acceptable, particularly in embodiments using a guide (e.g. 63, 69).

In order to meet these overall positioning tolerances, in embodiments without guide 76, blade fork assembly 60 is preferably constructed to position blade 66 within 0.03 mm, and even more preferably within 0.015 mm of an intended plane known with respect to the surfaces where fork 70 attaches to drive arm 140. In use with guide 76, blade fork assembly 60 is preferably constructed to position blade 66 within 0.3 mm, or more preferably within 0.15 mm, of an intended plane known with respect to the surfaces where fork 70 attaches to drive arm 140. However, it is within the scope of the present invention to permit tolerances twice as large as those enumerated as preferred.

Figure 6B:
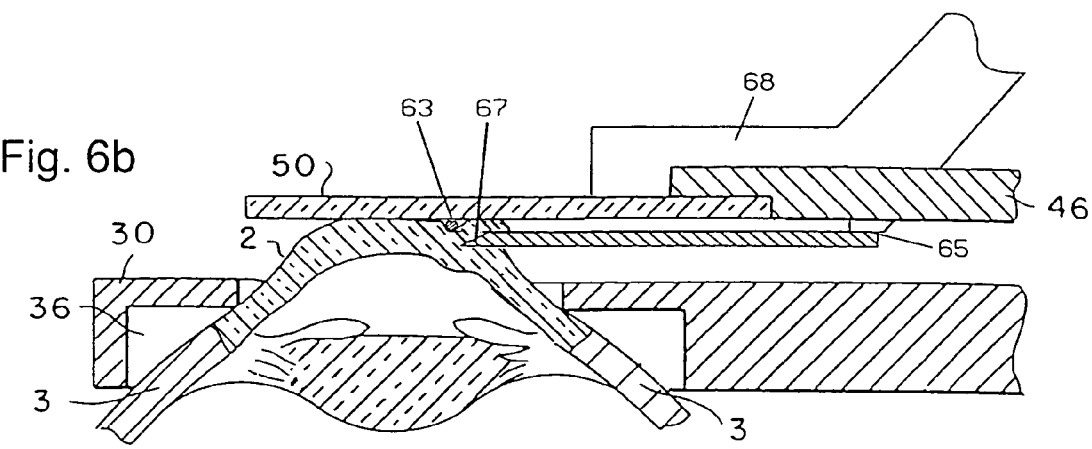
FIG. 6b is like FIG. 5a, except the blade has a guide which contacts the applanator.

In FIG. 6b, guide 63 leads just above blade 67, sliding between cornea 2 and applanator shoe 50. The spacing between guide 63 and blade 67 thus controls the corneal pocket wall thickness. The perimeter of the cross-section of guide 63 is advantageously small, preferably less than 2 mm or at least less than 6 mm. A small cross-sectional perimeter conveys several advantages: it reduces the frictional interaction between the guide and the cornea, it localizes a deformation of the cornea to avoid pressure on the eye generally, and it reduces the likelihood of trapped bubbles distorting the cornea to cause inaccurate cuts.

Figure 6C:
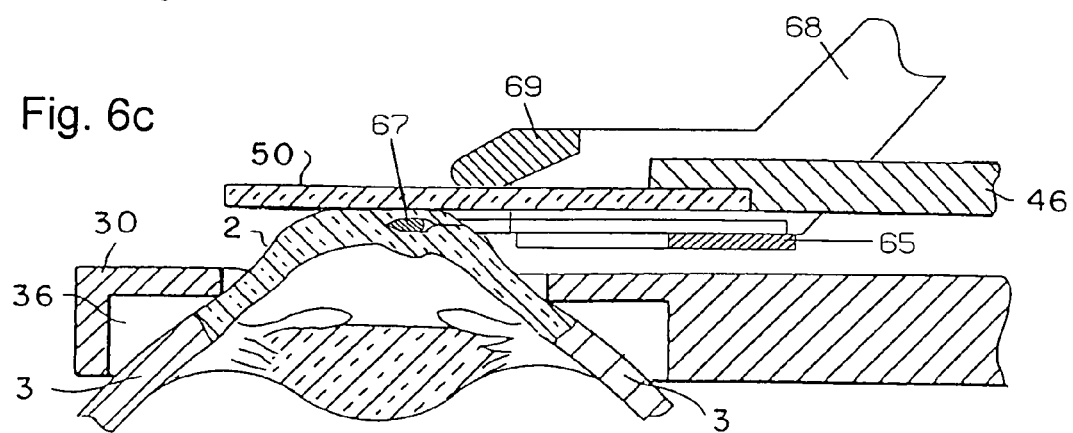
FIG. 6c shows a blade assembly with a guide contacting the obverse side of the applanator.

In FIG. 6c, guide feature 69 rides along the obverse side of applanator shoe 50 opposite cornea 2. The spacing between guide feature 69 and blade 67, along with the thickness of applanator shoe 50, thus control the corneal pocket wall thickness. It should be noted here that in some instances it may be desirable to contour a thickness of the corneal pocket. By shaping the thickness of applanator shoe 50 where it contacts cornea 2, and guiding blade 67 from a flat obverse side of applanator shoe 50 as shown, the thickness of the resulting pocket can be shaped as desired (the pocket wall thickness will be inverse to the corresponding applanator shoe thickness).

Figure 6D:
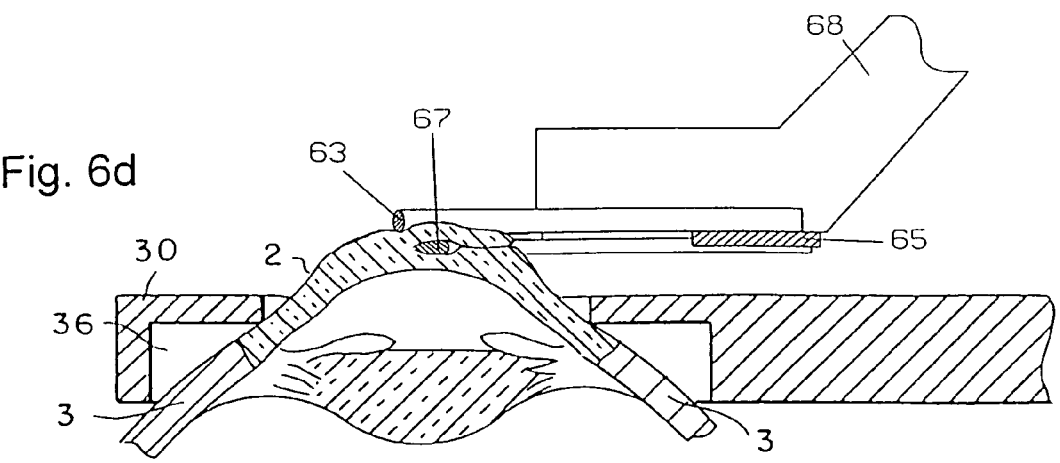
FIG. 6d shows a blade assembly and guide cutting a corneal pocket without an applanator.

FIG. 6d shows an embodiment in which the applanator is not used. Guide 63 provides a controlled spacing from blade 67 which in turn controls the corneal pocket wall thickness. In FIGS. 6c and 6d, the corneal tissue of the pocket can be seen returning to contact after passage of blade 67. In this embodiment, of course, distance tolerances to an applanator surface reference plane are of no concern.

Blade and Guide Construction

Figure 8A:
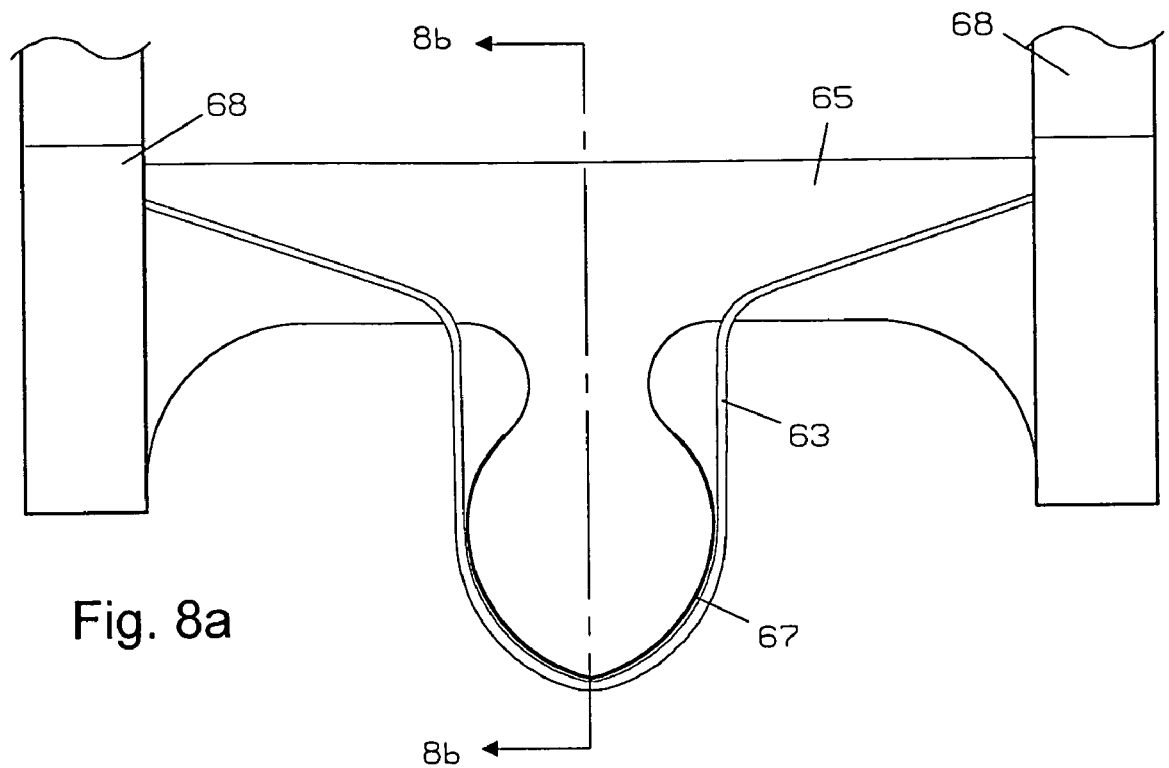
FIG. 8a details an embodiment of a corneal pocket blade with guide.
Figure 8B:
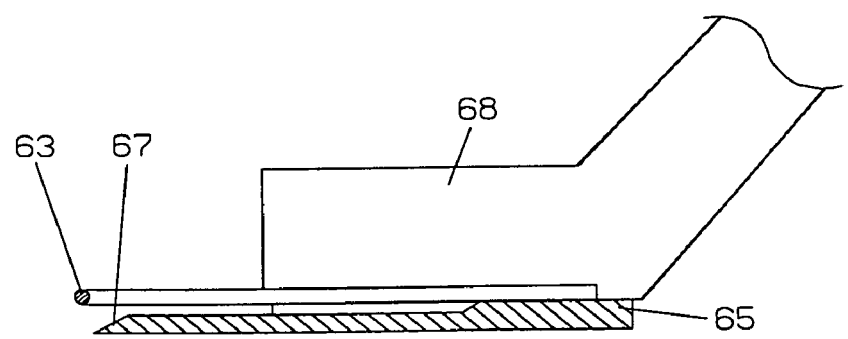
Figure 8C:
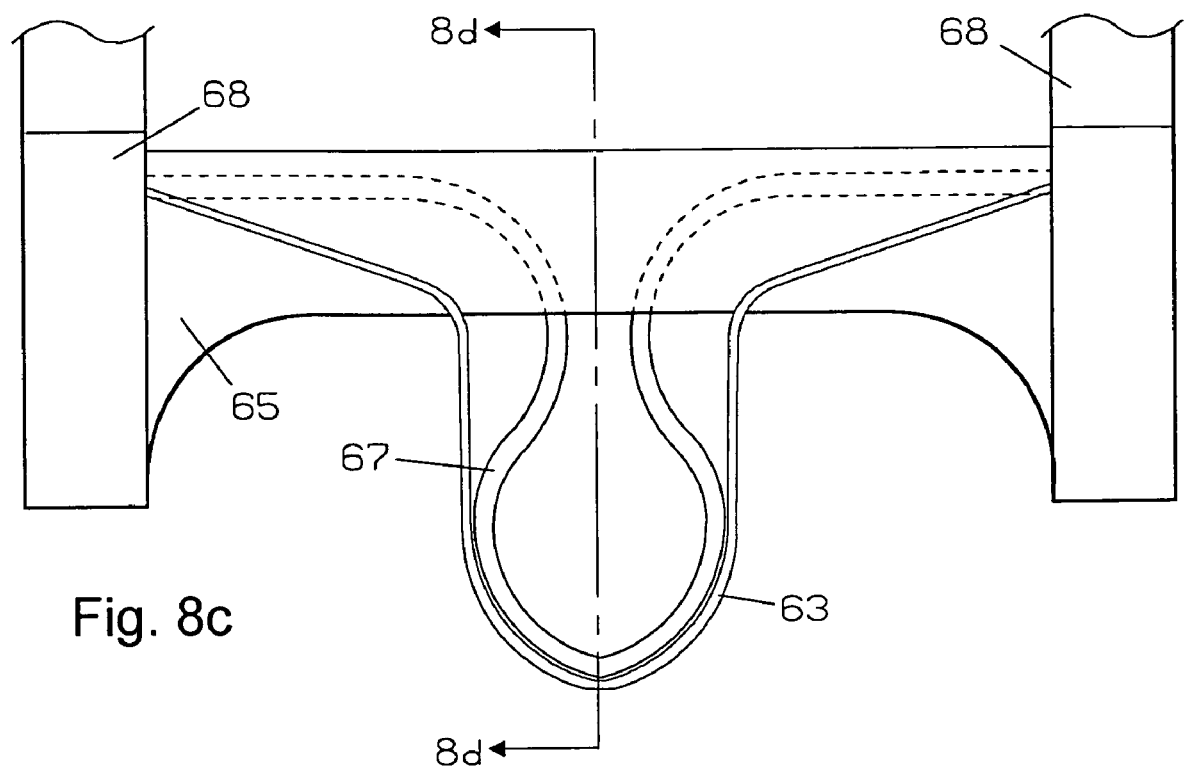
FIG. 8c details a blade having only a circumferential cross-section, with a guide.
Figure 8D:
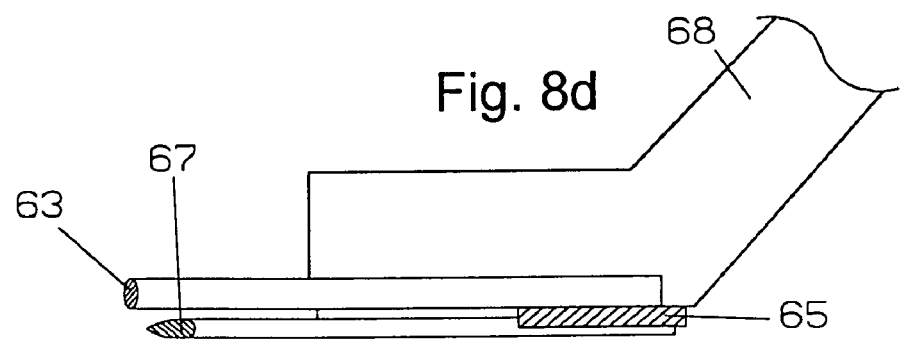
FIG. 8d is a section view of FIG. 8c.

FIGS. 8a–8g show details of various blade constructions. Blade support 65 in each figure is suspended between blade fork arms 68, though any means of supporting the blade accurately may be used. As shown in FIG. 8a and sectional view FIG. 8b, blade 67 may be simply an edge on stainless steel blade support 65, or may be a separate material, such as sapphire, bonded to support 65. Blade guide 63 preferably follows the cutting edge contours of blade 67. The angle shown for the edge of blade 67 helps to reduce blade drift, at least in the case where corneal tissue is distorted by the passage of guide 63 as can be seen in FIG. 6b. However, various blade edge geometries may be used depending on the overall surgical cutting circumstances FIG. 8c, with sectional view FIG. 8d, shows blade 67 formed as a narrow edge, rather than continuous with blade support 65. In this particular embodiment, blade strip 67 is attached by glue or welding to one side of blade support 65, while blade guide 63 is similarly attached but to the opposite side of support 65. However, any method effecting proper spacing between blade and guide is satisfactory. Both blade and guide may, for example, be stainless steel. Blade guide 63 in this embodiment have an oval cross section to increase strength to match that of blade 67. This embodiment is preferred for forming corneal pockets without using an applanator, and the alternative edge of blade 67 shown is effective with the correspondingly reduced of corneal tissue distortion of that method.

Figure 8E:
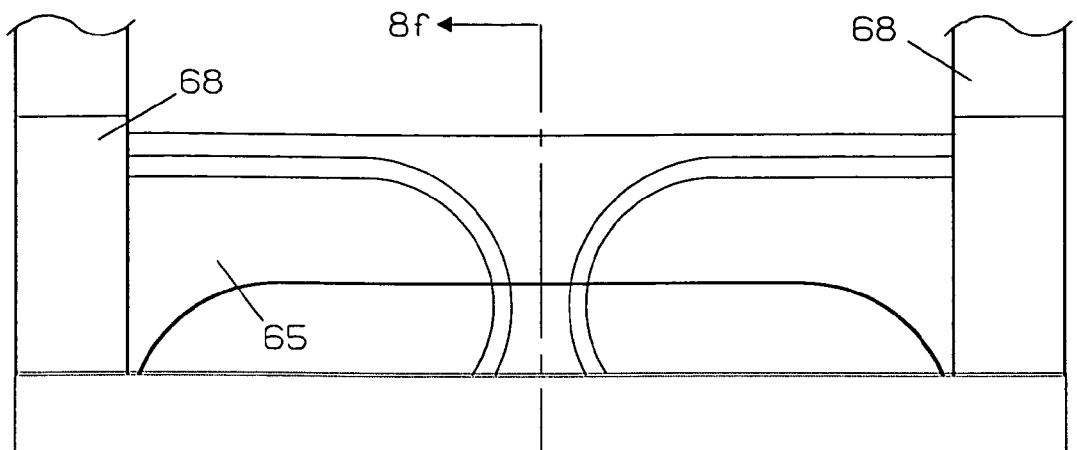
FIG. 8e details a blade on a blade fork assembly with an applanator obverse guide.
Figure 8F:
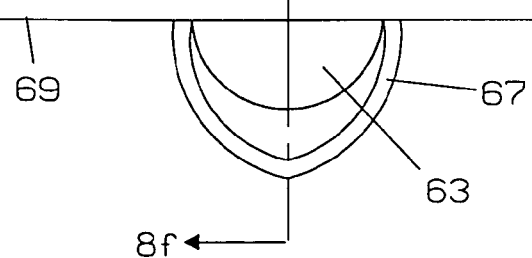
FIG. 8f is a section view of FIG. 8e.

FIG. 8e and sectional view FIG. 8f detail blade construction for cutting as shown in FIG. 6c. Guide feature 69 rests across the top side of blade support arms 68, and protrusion 70 rests on the obverse side of applanator shoe 50 (FIG. 6c). There is no guide near to blade 67 in this embodiment. Although not shown, one skilled in the art will have no difficulty understanding that guide feature 69 may be made readily removeable to allow access to the eye being operated on (after also moving the applanator, as described later).

Figure 8G:
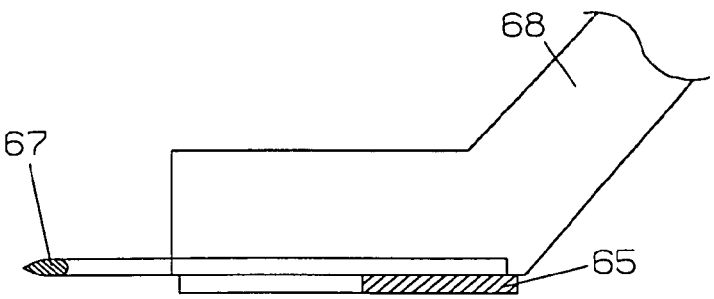
FIG. 8g is a section view of a blade without a guide.

FIG. 8g is very similar to FIG. 8f, with guide 69 removed. In this configuration, corneal pockets may be made accurately by a precision surgical unit and precision cutting head elements, without a need for a guide at all. Blade 67 is supported by blade support fork arms 68, which are driven by the surgical unit which also supports the applanator.

Applanator Assembly

Figure 9A:
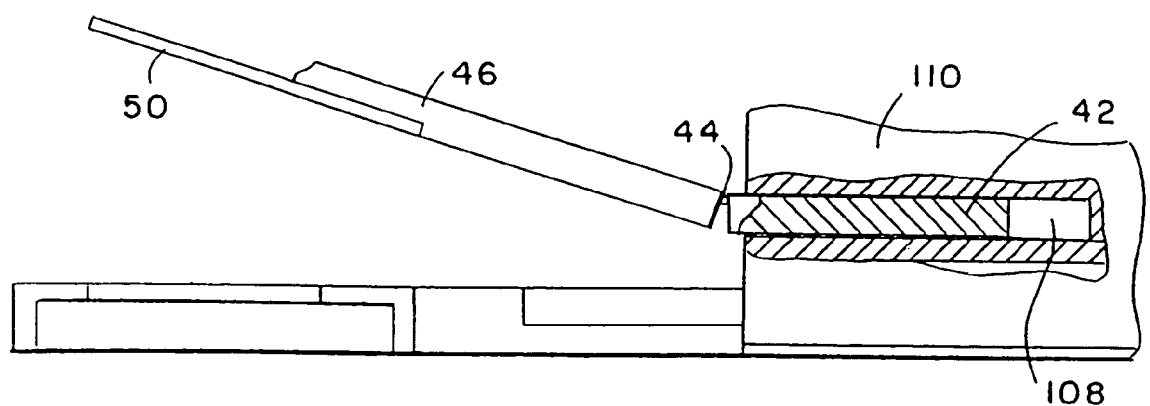
FIG. 9a shows an applanator extended and swung up and away from the positioning ring.
Figure 9B:
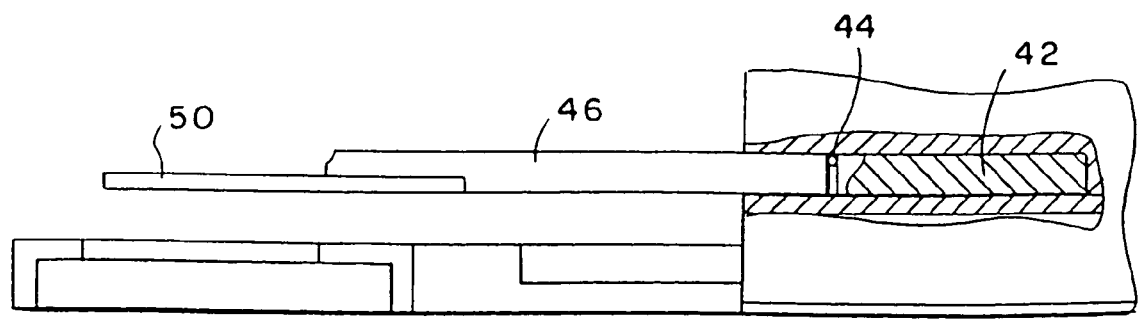
FIG. 9b shows the same applanator in the fully restrained position.

Referring to FIGS. 5, 6a, 9a, 9b and 10a, applanation shoe 50 is that part of applanator assembly 40 which includes the surface for restraining the cornea during incisions. Applanator assembly 40 as shown in FIGS. 5, 9a and 9b includes applanator retention insert 42, optional hinge 44, applanation shoe support 46, and applanation shoe 50. Applanation shoe 50 is preferably made of a transparent and abrasion-resistant material such as glass or sapphire, and marked with crosshair 52, to make the cutting operation visible to the surgeon. If the applanator is not hinged, then insert 42 and support 46 may be subparts of the same part.

Figure 11A:
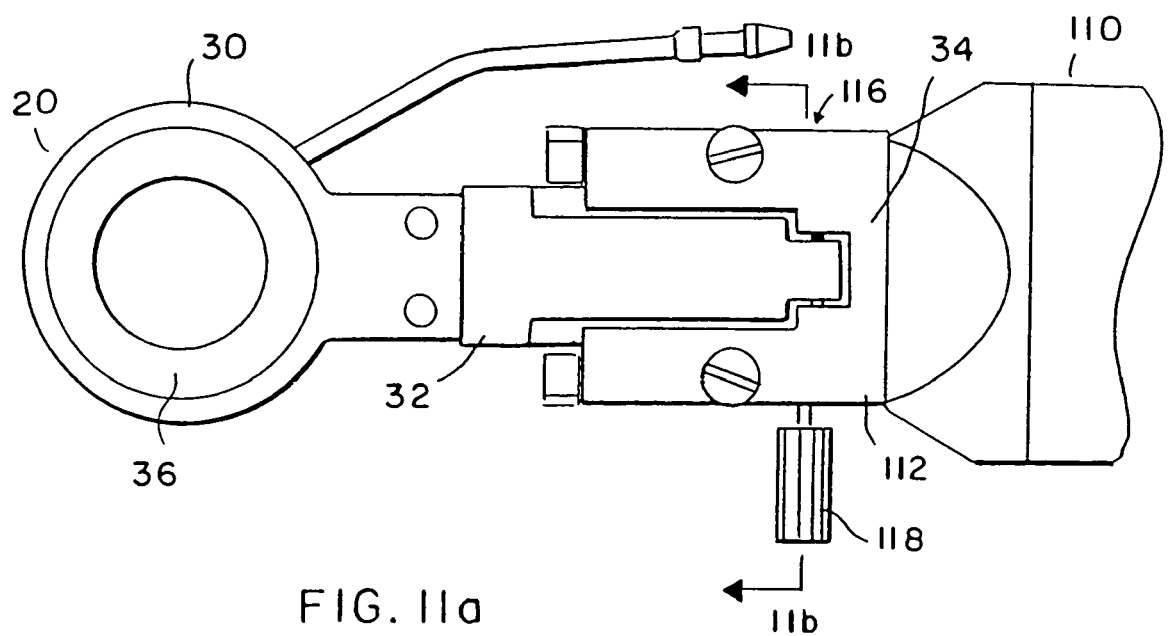
FIG. 11a shows the positioning ring attached to the drive assembly.
Figure 11B:
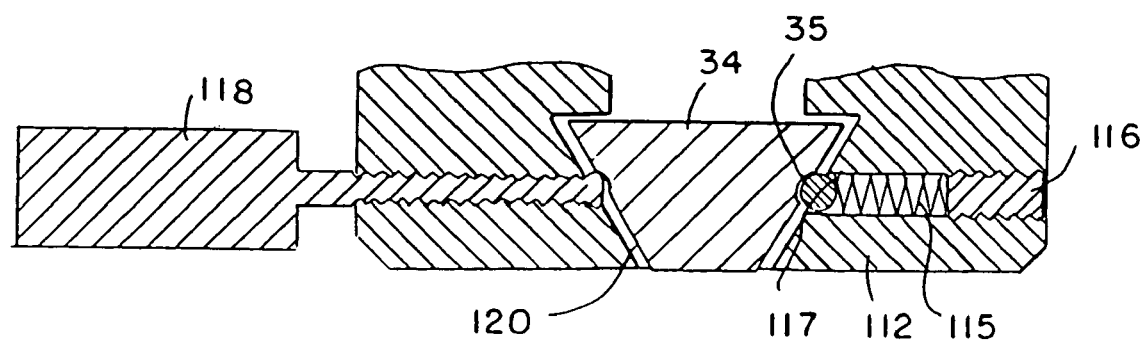

Applanator retention insert 42 and shoe support 46 preferably have trapezoidal edges, and slide into mating recess 108 of drive assembly 110, where they are located by a threaded captive-ball spring assembly on one side, and secured by thumbscrew 114 on the other side, in a manner similar to that described below in regard to positioning ring retention feature 34 of positioning ring assembly 20 (FIG. 11b).

As discussed above with respect to blade fork assembly 60, various materials may be used to construct applanator retention insert 42, applanation shoe support 46, and applanation shoe 50. For versions in which a guide 76 does not contact applanation shoe 50, abrasion resistance is less important. As above, the material chosen must be compatible with the method to be used to assure sterility of the element, whether a method such as heat, steam, gas, or gamma is used, or the element is sterile disposable. All of the same materials as for blade fork assembly 60 may be used, including preferably clear materials for applanation shoe 50.

Applanator assembly 40 is preferably able to swing out of the way to expose the cornea of an eyeball held in the retaining ring 30. One preferred mechanism to permit such swinging is shown in FIGS. 9a and 9b. In FIG. 9a, applanator assembly 40 is partly withdrawn from recess 108 in drive assembly 110 into which it is mounted, so that hinge 44 is exposed and applanation shoe 50, along with support 46, is enabled to swing up, preferably about 60 degrees, relative to applanator retention insert 42 which remains in recess 0.108. In FIG. 9b, applanator assembly 40 is fully home so that hinge 44 is captive in recess 108. Applanator assembly 40 is secured to drive assembly 110 by thumbscrew 114, which impinges on applanator retention insert 42.

Figure 10A:
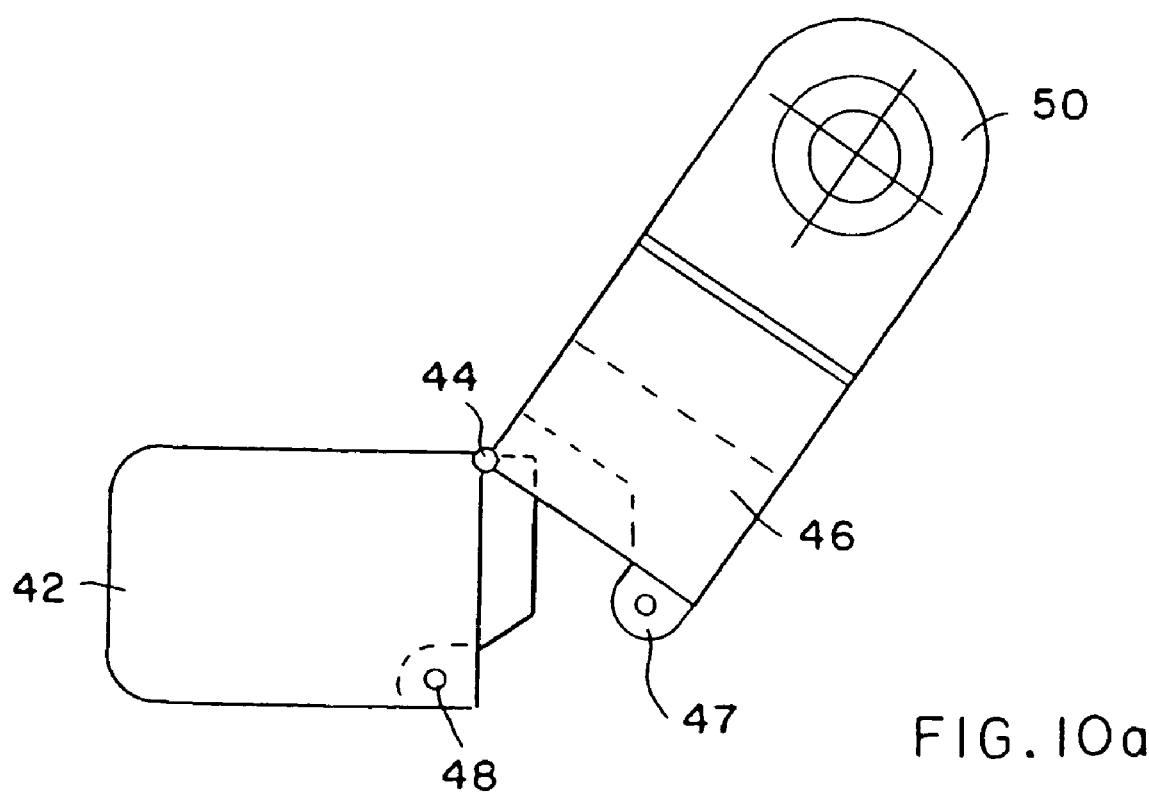
FIG. 10a shows an alternative method of swinging the applanator away.
Figure 10B:
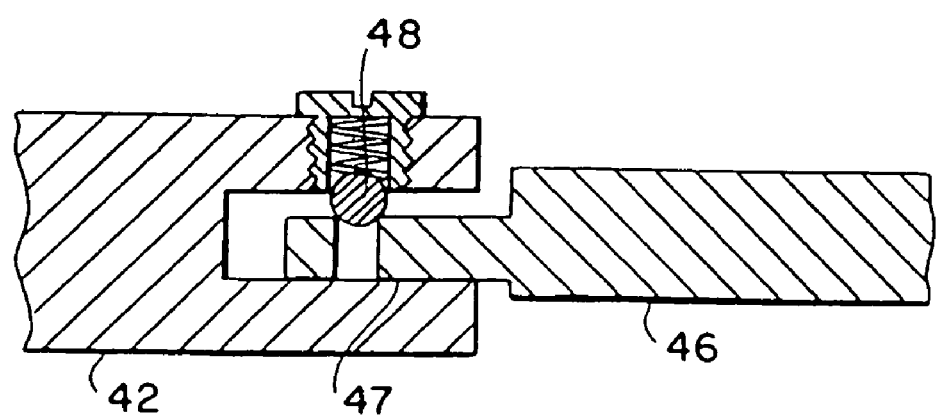

A second preferred embodiment to enable swinging is shown in FIG. 10a. There, hinge 44 permits applanation shoe 50 and support 46 to pivot away from applanator retention insert 42 while remaining in the same plane as insert 42. FIG. 10a shows shoe 50 with support 46 pivoted away from applanator retention insert 42, exposing latch feature 47. When closed, latch feature 47 will engage spring ball 48, thereby releasably securing the applanator in the closed position. FIG. 10b shows a cross-sectional detail of engaged latching mechanism 48.

The corneal restraining surface of applanation shoe 50 may be perfectly flat, or it may be contoured. The blade is generally guided a controlled distance from a "surface reference plane" of the applanation shoe, which is the plane which "just touches" the corneal restraint surface, and which is parallel to the desired cutting plane.

Positioning Ring Assembly

FIGS. 11a and 11b depicts details of positioning ring assembly 20. Positioning ring 30 is provided with vacuum to vacuum chamber 36 so that an eyeball placed against it may be drawn in, distending the cornea which is then typically pressed against applanation shoe 50 as shown in FIGS. 7a–7d. The vacuum is furnished through vacuum connection tube 22, with the vacuum hose (not shown) placed over vacuum connection nipple 24 and stopped by vacuum tube stop 26. Alternatively, vacuum may be ducted through ring support 32 and drive assembly 110 to obviate vacuum connection tube 22, the vacuum hose 412 connected then only to drive assembly 110 and optimally consolidated with electrical control cable 410.

Referring to FIG. 11a, which is a bottom view, and cross-section FIG. 11b, positioning ring support 32 preferably includes retention feature 34 having detent 35. Retention feature 34 slides into matching recess 120 in drive assembly 110. Captured ball 117 settles into detent 35 under the pressure of captured spring 115 to properly locate positioning ring assembly 20. Then, thumbscrew 118 secures retention feature 34, seating it firmly against the sides of recess 120 formed in head 112 of drive assembly 110. (Note that FIG. 11a omits thumbscrew 114, located in head 112 opposite thumbscrew 118, and used for securing the applanation assembly.)

As discussed with regard to blade fork assembly 60 and applanator 40, a variety of materials may be used for positioning ring 20. The choice depends on whether sterility is to be ensured by reuse of the element in conjunction with a sterilization method, or by using sterile disposable elements. Suitable materials include metals, such as stainless steel, and plastics, such as polycarbonate, polysulfone, polypropylene or others.

Drive Assembly

Figure 12:
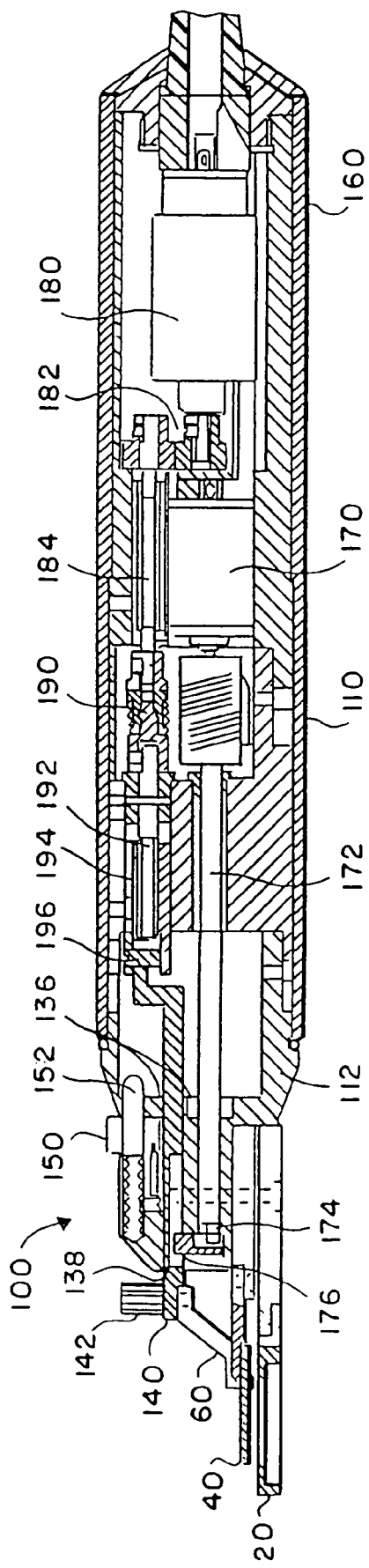
FIG. 12 shows a cross-section of a surgical unit using motor driven blade oscillation.
Figure 13:
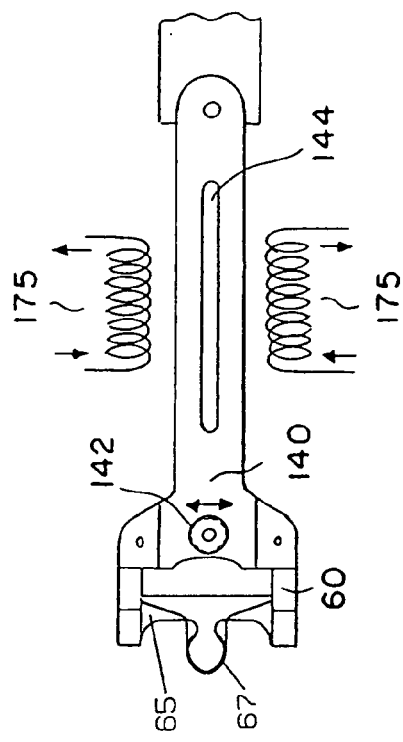
FIG. 13 shows alternative features for the surgical unit to permit field-driven blade oscillation.

FIGS. 12 & 13 show details of a preferred embodiment for surgical unit 100, and in particular shows details of a preferred embodiment for drive assembly 110, which is largely enclosed by drive assembly cover 160.

Referring to FIG. 12, the primary actuators within drive assembly 110 are travel motor 180 and oscillation motor 170. Travel motor 180 drives shaft 184 through gear train 182. Clutch 190 couples a limited torque to screw 192. The rotational motion of screw 192 is converted to linear motion by threaded traveller 194. Pivot assembly 196 couples the motion from the forward end of traveller 194 to blade fork drive arm 140, while permitting drive arm 140 to oscillate rotationally about the pivot of pivot assembly 196. Blade travel stop adjust knob 150 preferably rotates a threaded member which adjustably stops blade fork drive arm 140 travel.

Drive arm 140 preferably includes portions of its top and bottom surface which are made closely parallel to each other and a controlled distance apart (the top and bottom surfaces are those most distal from the center of drive arm 140 in the direction parallel to the pivot axis of pivot assembly 196, with the top surface being the farther from positioning ring 30). Drive arm 140 top and bottom surfaces are preferably flat to within 0.005 mm over their travel range of 1.5 cm, and are slidably captured by bearing surfaces 136 and 138 of drive assembly head 112. The bearing surfaces limit top-to-bottom play of drive arm 140 to preferably 0.01 mm or even more preferably to 0.05 mm.

Drive assembly head 112 holds applanator assembly 40 and blade fork drive arm 140 such that blade 66 is maintained a known distance away from applanation shoe 50 as it travels, as described above in the section entitled "Blade Fork Assembly." The tolerances needed to establish precise relative positioning between the drive arm and the applanator mounting surface are preferably established by either placing shims, or by machining head 112 (see FIGS. 5, 6). This procedure may adjust either the position of bearing surfaces 136, 138 for drive arm 140, or the position of recess 108 for applanator assembly 40. Control of the actual blade travel and applanation shoe reference planes then further depends on the precise construction of those cutting head elements, discussed in their respective sections above. In embodiments utilizing guide 76 (not shown) parallel to blade 66 on blade fork 70, the distance between blade 66 and applanation shoe 50 is preferably controlled to within +/−0.5 mm, or more preferably within +/−0.25 mm.

Oscillation may be imparted to drive arm 140 by slider 176 which oscillates in a direction perpendicular to the page. Slider 176 interferes with the edges of a groove in drive arm 140, while the groove allows drive arm 140 to travel in and out of drive assembly 110. Slider 176 receives oscillation drive from oscillation motor 170 via shaft 172 and eccentric pin 174. Eccentric pin 174 rides in a slot in slider 176 which absorbs the vertical component of eccentric pin 174, but transmits the lateral motion.

In order to cause a widening opening to the corneal pocket, the oscillation lateral travel must be gradually increased through much of the blade forward travel. In this embodiment, oscillation motor 170 is preferably a stepper motor, which does not travel a full half circle, but rather reverses direction to form gradually increasing arcs.

FIG. 13 shows an alternative embodiment of means to impart oscillating motion to drive arm 140. In this embodiment drive arm 140 incorporates ferromagnetic material 144 which is acted on by magnetic fields generated by coils 175 positioned along the sides of drive arm 140. A position feedback sensor may be used to precisely control the amplitude of the lateral oscillation. In this embodiment, if position feedback is not used, then it is preferred that the drive arm lateral travel be controlled by an interference piece having a ramped shape which allows wider travel as the drive arm extends, so that travel is progressively less limited (i.e. has a progressively increasing amplitude) as the drive arm extends from surgical unit 100.

Surgical Device Alternative Embodiments

It will be appreciated by those skilled in the art that many alternative embodiments are envisioned within the scope of the present invention. Some possible variations of the blade fork assembly are discussed in the blade fork assembly section above. Variations of other parts are discussed below, but do not represent an exhaustive survey of possibilities; rather, they serve as examples to show that a wide variety of mechanisms are encompassed within the scope of the invention.

Myriad physical configurations of the connection interface surfaces which removably attach the blade fork assembly to the blade fork drive arm can provide the predictable positioning needed to practice the invention. The mating parts of the interface are described herein as trapezoidal or "dove-tail" but may take any form having locating features, including sawtooth, rectangular, eccentric oval, keyhole, or other shapes too numerous to enumerate.

Similarly, the means for securing the connection interface is shown herein as a thumbscrew, but may be a cam locking lever, or could be accomplished by means of: magnetic attraction, spring-loaded detents, or tapered engaging pieces fitted into a recess formed partly from each of the mating parts. Any method known in the art to disengageably secure two pieces in a closely predictable relationship could be used.

A preferred embodiment of the applanator includes a pivot so the applanator can be pivoted away from the cornea. Hinges and pivots of all known types are well within the scope of this invention. A flexible chain, cable, strap or string could retain the applanation shoe when the rigid attachment is disconnected; or the applanator could be made retractable.

Any blade fork can be used which is able to support the blade (and blade guide, if use) in a well-controlled position with respect to the mounting surface of the connection interface. The blade fork need not be a fork at all, but could support the blade from a single arm attached to the drive mechanism, rather than from dual arms.

A corneal support device may be a positioning ring, as discussed above, or an applanator, or some other device to prevent the eye from moving during surgery, while yet permitting access to the cornea by the corneal pocket blade. For example, a transparent cornea support device may be shaped somewhat like a baseball batting helmet, with the bill pointing toward the keratome drive mechanism to permit access into the corneal tissue, and the edges surrounding the corneal tissue and the sclera to securely restrain the eye. The inside of such corneal support device, against which the central portion of the cornea is disposed for cutting, is then shaped as described for the bottom of the applanator as described above. The top of such a corneal support device may be flat to accommodate a guide 69 for a corneal pocket blade as shown in FIG. 8f. Thus, a single cornea support device may function as both the presently preferred positioning ring and applanator together.

It is also possible to provide a corneal pocket blade assembly which is guided, for example, by following channels which are rigidly connected to a corneal support device. Thus the present invention is not necessarily limited to the blade and support structure which is described herein by way of example.

A preferred embodiment of this invention includes sterile disposable or sterilizable disposable cutting head elements. A non-limiting variety of material choices suitable for such an embodiment is discussed above with respect to each cutting head element. There is no need for the various cutting head elements to be all disposable or all permanent, but a mixture of types is also suitable.

User commands may be recognized in any known way, including voice command reception, and sensing user activation of sensors or switches located on the surgical unit or in other convenient places. The commands thus recognized may exert control through any combination of control elements, which may include mechanical means, direct electrical control, or intelligent electrical control with intelligence provided by any means known to the art. The command recognition and control elements could be physically located amy accessible place, and as an example could be placed largely or entirely within the surgical unit.

Lenses

FIGS. 14a–14e show several embodiments of lenses suitable for the present invention. It is not essential, but is preferred that the lens have a feature which will cause it to remain in the corneal pocket. In many instances, such as when astigmatism must be corrected, it is desirable that the lens retain the orientation it is given upon insertion.

Figure 14A:
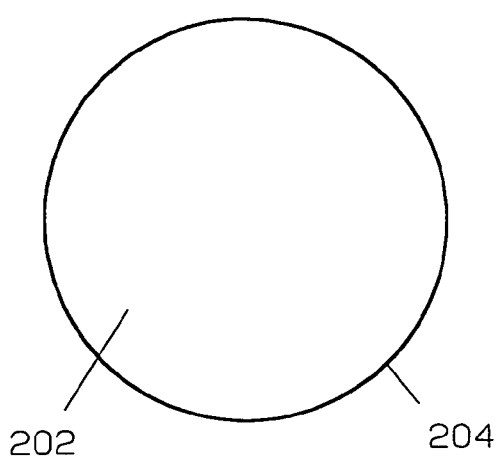
FIGS. 14a–14e show details of lenses according to the present invention.

FIG. 14a shows a lens having refractive material 202 within a generally circular shaped perimeter 204. In order to both transport oxygen and create a snug fit in a corneal pocket, it is desirable that this lens be made of a hydrophilic material which swells somewhat when hydrated. Such materials, for example hydrogels, are used in some present contact lenses. The lens may be inserted fully hydrated to elastically fit in the pocket, or while at least partly dehydrated such that subsequent hydration helps secure the fit in the pocket.

Figure 14B:
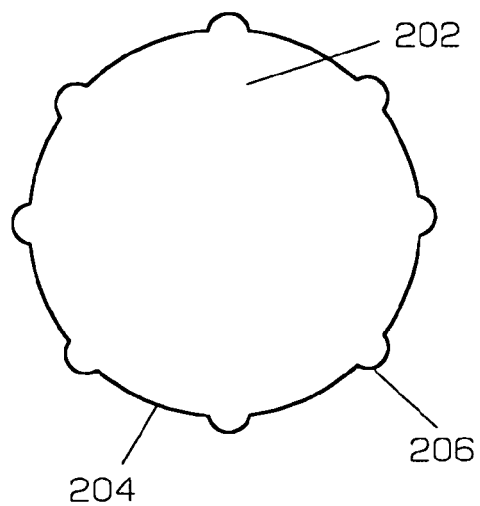
Figure 14C:
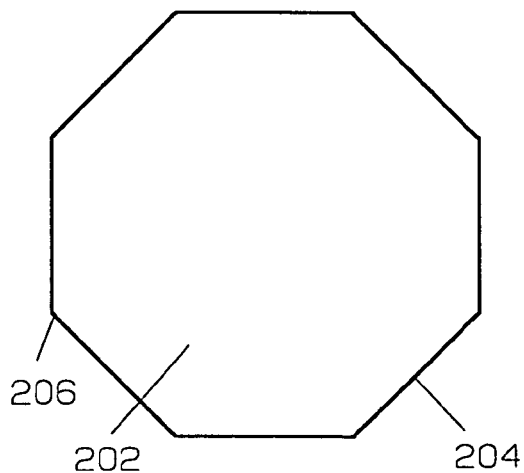
Figure 14D:
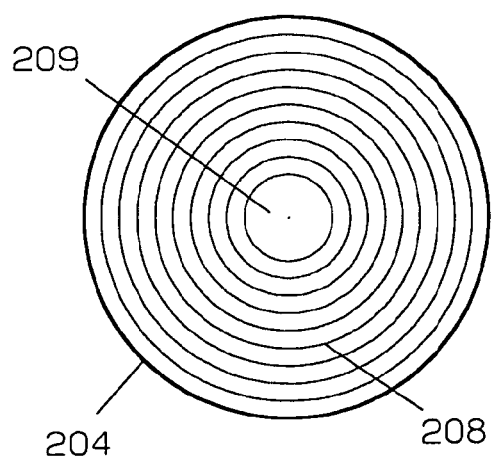

FIG. 14b shows a lens which is preferably semi-rigid, such that interference features 206 will interfere with corneal tissue and thus resist loss or movement within the corneal pocket. FIG. 14c shows an example of another shape which may be used to resist shifts in position after insertion. In practice, features 206 are not sharp.

The lenses shown in FIGS. 14a–14c are limited somewhat in the range of vision correction they can effect, due to their limited index of refraction, and limited thickness. Such lenses are particularly limited in their ability to correct presbyopia. The lens shown in FIG. 14c is a Fresnel lens, and includes an annular series of lens sections 208 between perimeter 204 and the central portion 209. Fresnel lenses may not be practical as contact-type lenses on the surface of corneas, due to their ridged surface, but may be used within corneal tissue where they cannot irritate epithelial surfaces. The greater range and control of refraction permitted by a Fresnel lens is particularly useful for correction of presbyopia by the method and apparatus of the present invention. Of course, a Fresnel lens may also be given retention features as shown in FIGS. 14b and 14c; and the annular ridges of the Fresnel lens will themselves resist lateral displacement.

Lenses having a single focal length are generally sufficient to correct simple myopia or hyperopia, and may of course be used to practice the present invention. However, lenses having variations in either refractive index or lens shape, or both, may be used advantageously as part of the present invention to establish a multifocal lens. The focal length of such lens is not constant, but varies across the expanse of the lens. Such multifocality can be used to compensate for presbyopia, by causing one portion of the light incoming to the eye to be focussed if the source is far away, while another portion of the light is focussed when the source is close (as when reading). Varying focal length of toric surfaces of the lens can be used to correct astigmatism. The present invention may be practiced using multifocal lenses to simultaneously correct or compensate various combinations of defects including myopia, hyperopia, astigmatism and presbyopia.

The effectiveness of such varying focal length lenses relies upon reliable positioning of the lens, as is provided by the present invention, in order to avoid misalignment of the lens, and to simplify adaptation to a plurality of focal lengths by the visual processing facilities. For example, presbyopia may be compensated by situating a small area, preferably less than 3 mm diameter, of focal-length reducing lens at the center of the cornea. Such location will have greater effect in high-light conditions (as are typical for reading), when the pupil is small, and proportionally less effect under lower lighting conditions, such as night driving, when the pupil is large. Thus the lens location with respect to the pupil must be maintained; and the brain will adapt more easily to a non-uniform focus of the eye which is at least constant.

Figure 14E:
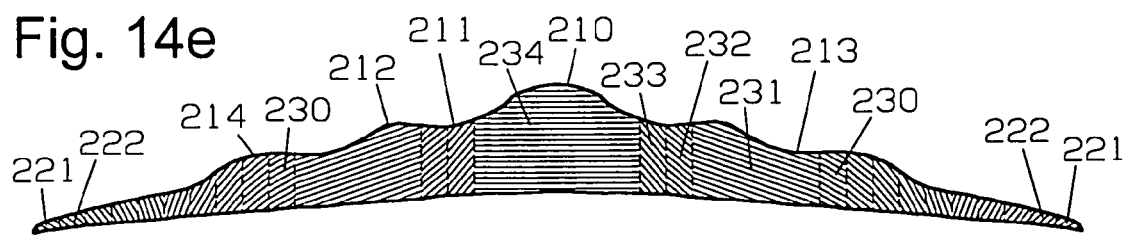

Multifocality may be accomplished using a Fresnel lens, as described above, or using a non-Fresnel lens having a varying refractive shape and/or a varying refractive index. A non-Fresnel lens having both varying refractive index and also varying refractive shape is shown in cross section in FIG. 14e. The lens of FIG. 14e is preferably made of hydrogel material, and the refractive index of the material is changed in annular rings from outer annular ring 221 to central portion 234. (A top view of such a lens would appear very much as FIG. 14d; the lines between annular sections would be present, but not visible.)

The refractive index of the lens material varies slightly between each adjacent annular section of the lens, for example by changing the water content of the lens as is known. For example, outermost annular ring 221 may have a very high water content, and a refractive index of approximately 1.37 (to match that of the surrounding corneal tissue). Innermost section 234 of the lens has a lower water content, and a refractive index of approximately 1.46. In between, the refractive index changes between adjacent sections in about 0.01 refractive index steps. Thus, the refractive index of annular ring 221 is about 1.37, that of second outermost ring 222 is 1.38, and the increase continues at each annular ring until by annular ring 230, the index of refraction is about 1.46. This higher index enhances the refraction of feature 214 so that a shorter focal length is effected by that feature. Next, the indices of refraction of annular ring 231 is about 1.445, of ring 232 about 1.43, and of ring 233 about 1.445, and of central portion 234 about 1.46 as mentioned above. Representative dimensions for the lens of FIG. 14e are 0.9 mm diameter for central section 234; 0.15 mm radius for each of annular rings 221–220 and 232–233; and 0.75 mm radius for annular section 231.

The variations in refractive index across the lens may enhance the focal length variations caused by lens contour features such as 210, 211, 212, 213 and 214. For example, feature 210 provides a focal-length reducing section at the center of the cornea, which, as described above, is desirable to compensate for presbyopia by yielding an area of 'reading' focus at the center of the pupil, and this effect is enhanced by the relatively high refractive index of central portion 234. Features 212 and 214 may provide further rings of short focal length, or may be part of a toric variation of focus to compensate for astigmatic defects of the subject eye, and their effects may again be aided by the corresponding variations in refractive index of the lens material. It will be understood by those skilled in the art that the actual choice of refractive contour depends upon the defects of the eye to be corrected, and that FIG. 14e merely demonstrates combinations of refractive index and contour variations.

Variation in refractive index down to that of corneal tissue, as described, has a particular advantage in reducing edge glare effects. Light bounces off the edges of lenses (interfaces having a substantial discontinuity of index of refraction where light hits at a shallow angle), and may cause glare as this essentially random light enters the eye. However, by establishing the lens edge at an index of refraction matching that of the surrounding corneal tissue, such reflected or bouncing light, and the resulting glare, may be reduced or eliminated.

The annular rings of varying refractive index may be established by application of successive layers of material to form a tubular section of lens material, from which individual lenses will be cut. After each successive layer of material is disposed on the core, crosslinking of the lens material of adjacent sections should be effected to unify the sections; this may be accomplished, for example, using ultraviolet or other high energy irradiation. In the lens of FIG. 14e, exemplary dimensions include central portion 216 (high index material) having a diameter of 3 mm. Ten annular rings, each 0.15 mm thick, step the refractive index down to that of the cornea over a radius of 1.5 mm, so that the overall diameter of this lens is 6 mm.

Exemplary embodiments of the invention are disclosed herein. The invention is not to be limited to those embodiments, but is defined by the claims which follow.

What is claimed is:

1. A corneal-pocket keratome, comprising:
 a corneal-pocket blade assembly having a corneal-pocket blade supported by a blade support assembly, the blade having a cutting edge on a portion of the blade which is cantilevered from the blade support assembly to protrude therefrom;
 a keratome drive mechanism supporting the corneal-pocket blade assembly, the drive mechanism including
 a primary drive mechanism to drive the blade assembly in a primary path of travel generally perpendicular to a focal axis of the eye, and
 a lateral drive mechanism to impart movement to the blade assembly in a direction lateral to the primary path of travel; and
 a corneal restraint device attached to the keratome drive mechanism.

2. The corneal-pocket keratome of claim 1 wherein the primary path of travel is a single direction.

3. The corneal-pocket keratome of claim 1, wherein the lateral drive mechanism is controllable to vary a length of lateral movement of the blade assembly.

4. The corneal-pocket keratome of claim 1, wherein the lateral drive mechanism increases a length of lateral movement of the blade assembly as the blade assembly proceeds in the forward direction of travel.

5. The corneal-pocket keratome of claim 1, wherein the lateral drive mechanism imparts a laterally oscillating movement to the blade assembly.

6. The corneal-pocket keratome of claim 1, wherein the corneal-pocket blade support includes a corneal pocket wall-thickness guide to control a corneal-pocket outer wall thickness.

7. The corneal-pocket keratome of claim 6, wherein the corneal-pocket wall-thickness guide includes a guide edge, the guide edge substantially matching a shape of a portion of the cutting edge of the corneal-pocket blade protrusion and being disposed at a controlled distance from said portion of the cutting edge.

8. The corneal-pocket keratome of claim 6, wherein the corneal-pocket wall-thickness guide is disposed in sliding contact with the corneal restraint device.

9. The corneal-pocket keratome of claim 8, wherein the corneal-pocket wall-thickness guide is disposed in sliding contact with an applanation shoe side opposite a cornea-restraining side of the applanation shoe.

10. The corneal-pocket keratome of claim 1, wherein the corneal restraint device is a corneal support shoe for supporting a cornea of the subject eye.

11. The corneal-pocket keratome of claim 1, further including a cornea positioning ring for restraining the cornea of the subject eye.

12. The corneal-pocket keratome of claim 11, further including a positioning ring retention feature having a finger-operable mechanism to release the positioning ring from the keratome drive mechanism by finger manipulation without a need for tools.

13. The corneal-pocket keratome of claim 1, further including a corneal restraint device retaining feature which is engageable and releasable by finger manipulation without a need for tools.

14. The corneal-pocket keratome of claim 1 wherein the corneal restraint device is pivotably disengageable from the cornea.

15. A corneal-pocket blade assembly for use in the corneal-pocket keratome of claim 1, comprising a corneal-pocket blade to be cantilevered from the blade support assembly so as to protrude therefrom, and having a cutting edge on a portion of the cantilevered blade distal from the blade support assembly.

16. A corneal restraint device for use in the corneal-pocket keratome of claim 13, including a mating feature engageable with said corneal restraint device retaining feature.

* * * * *